United States Patent

Koshigoe et al.

[11] Patent Number: 5,488,118
[45] Date of Patent: Jan. 30, 1996

[54] PROCESS FOR PRODUCING OPTICALLY ACTIVE ERYTHRO-3-AMINO-1,2-EPOXY COMPOUND

[75] Inventors: Taichi Koshigoe, Higashimatsuyama; Hitoshi Satoh, Saitama; Kenichi Yamamoto, Yono, all of Japan

[73] Assignee: Nippon Kayaku Kabushiki Kaisha, Tokyo, Japan

[21] Appl. No.: 345,074

[22] Filed: Nov. 28, 1994

[30] Foreign Application Priority Data

Dec. 6, 1993 [JP] Japan ................................. 5-339158

[51] Int. Cl.$^6$ ..................... C07D 301/00; C07D 303/36; C07C 229/34
[52] U.S. Cl. ................................ 549/518; 558/48
[58] Field of Search ................. 549/518; 558/48

[56] References Cited

U.S. PATENT DOCUMENTS 5,179,212  1/1993  Takahashi et al. ................. 558/48

FOREIGN PATENT DOCUMENTS 0346847  12/1989  European Pat. Off. .
0432694  6/1991   European Pat. Off. .
0430096  6/1991   European Pat. Off. ........ 549/518
0455473  11/1991  European Pat. Off. ........ 549/518
8910350  11/1989  WIPO ................. 549/518

OTHER PUBLICATIONS

Journal of Organic Chemistry, vol. 50, (1985) pp. 4615–4625.

*Primary Examiner*—Joseph E. Evans
*Attorney, Agent, or Firm*—Nields & Lemack

[57] ABSTRACT

The present invention relates to a process for producing an optically active erythro-3-amino-1,2-epoxy compound represented by the following general formula (3):

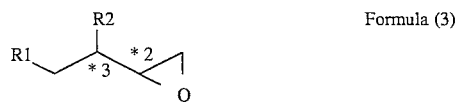

Formula (3)

wherein R1 represents a hydrocarbon residue having 3 to 12 carbon atoms; and R2 represents optionally protected amino, provided that when the carbon atom at the *3-position has an S configuration, then the carbon atom at the *2-position has an S configuration, and when the carbon atom at the *3-position has an R configuration, then the carbon atom at the *2-position has an R configuration.

20 Claims, No Drawings

PROCESS FOR PRODUCING OPTICALLY ACTIVE ERYTHRO-3-AMINO-1,2-EPOXY COMPOUND

FIELD OF THE INVENTION

The erythro-3-amino-1,2-epoxy compounds according to the present invention have been used as a starting material for synthesizing medicinal intermediates. For example, they are employed as a useful intermediate in the synthesis of an HIV protease inhibitor (see EP 432694 etc.).

BACKGROUND OF THE INVENTION

Known methods for producing erythro-3-amino-1,2-epoxy compounds include the following ones:

(1) a method comprising reacting an (S)-α-aminopropanal derivative, which has been synthesized from an (S)-α-amino acid, with dimethylsulfonylmethylide [see J. Org. Chem., 50, 4615–4625 (1985)];

(2) a method comprising reducing an (S)-3-amino-1-chloro-2-butanone derivative, which has been synthesized from an (S)-α-amino acid, with a ketone followed by cyclization (see EP 346847); and (3) a method wherein the reaction proceeds via (S)-3-amino-2-substituted-1-butanol which has been synthesized from an (S)-α-amino acid (see EP 432694).

In the above methods, however, it is generally needed to construct a novel asymmetric carbon atom and the reaction cannot usually proceed stereo-specifically. Accordingly it is unavoidable that unnecessary diastereomer(s) are thus formed. In fact, the above methods each achieves only a poor selectivity. To obtain a desired product with a high optical purity, therefore, optical purification procedures (for example, optical resolution or silica gel chromatography) are effected, which results in a low yield and a poor operating efficiency. Thus these methods are hardly regarded as a practically usable one.

SUMMARY OF THE INVENTION

Under these circumstances, the present inventors have conducted extensive studies and consequently found out a process for improving the above-mentioned disadvantages.

Accordingly, in the first aspect, the present invention relates to a process for producing an optically active erythro-3-amino-1,2-epoxy compound represented by the following general formula (3):

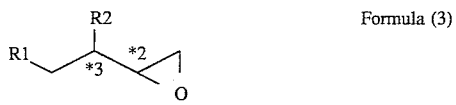

Formula (3)

wherein R1 represents a hydrocarbon residue having 3 to 12 carbon atoms; and R2 represents optionally protected amino, provided that when the carbon atom at the *3-position has an S configuration, then the carbon atom at the *2-position has an S configuration, and when the carbon atom at the *3-position has an R configuration, then the carbon atom at the *2-position has an R configuration, characterized by reducing an optically active threo-3-amino-2-substituted butyrate derivative represented by the following general formula (1):

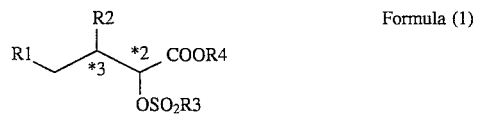

Formula (1)

wherein R1 and R2 are each as defined above; R3 represents a hydrocarbon residue having 1 to 12 carbon atoms; and R4 represents an ester residue, provided that when the carbon atom at the *3-position has an S configuration, then the carbon atom at the *2-position has an R configuration, and when the carbon atom at the *3-position has an R configuration, then the carbon atom at the *2-position has an S configuration, and then epoxidizing the obtained optically active threo-3-amino-2-substituted-1-butanol derivative represented by the following general formula (2):

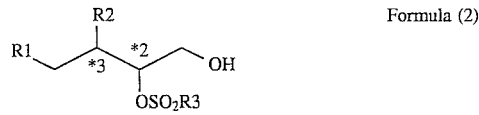

Formula (2)

wherein R1, R2, *2 and *3 are each as defined above, in the presence of a base to thereby give the target compound of the general formula (3).

In the second aspect, the present invention relates to an optically active threo-3-amino-2-substituted-1-butanol derivative represented by the following general formula (4):

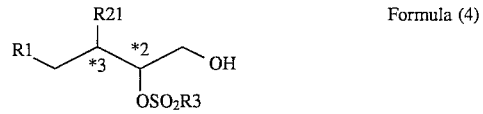

Formula (4)

wherein R1 represents a hydrocarbon residue having 3 to 12 carbon atoms; R21 represents an optionally protected amino except phthalimino; and R3 represents a hydrocarbon residue having 1 to 12 carbon atoms, provided that when the carbon atom at the *3-position has an S configuration, then the carbon atom at the *2-position has an R configuration, and when the carbon atom at the *3-position has an R configuration, then the carbon atom at the *2-position has an S configuration. The term "optionally protected" in the present invention means "protected or unprotected".

According to the present invention, an erythro-3-amino-1,2-epoxy compound having a desired configuration can be selectively and efficiently obtained in a high yield by using a threo-3-amino- 2-hydroxy-butyric acid derivative as a starting compound.

DETAILED DESCRIPTION OF THE INVENTION

As the hydrocarbon residue having 3 to 12, preferably 3 to 8, carbon atoms represented by the group R1 in the general formulae (1) to (3) in the present invention, either saturated or unsaturated, linear or cyclic ones or combinations thereof are usable. As particular examples thereof, alkyl, aryl and aralkyl groups may be cited. These hydrocarbon residues optionally have substituents which do not affect the present reaction. The preferable alkyl groups include those having 3 to 8 carbon atoms such as n-propyl, isopropyl, n-butyl, isobutyl, sec-butyl, tert-butyl, pentyl and hexyl groups. The cycloalkyl groups include cyclopropyl, cyclobutyl, cyclopentyl and cyclohexyl groups. The aryl groups include optionally substituted phenyl and naphthyl groups such as phenyl, lower alkyl-substituted phenyl such as p-tolyl, lower alkoxy-substituted phenyl such as 4-methoxyphenyl, halogen-substituted phenyl such as 4-chlorophenyl, 1-naphthyl and 2-naphthyl groups. The terms "lower alkyl" and "lower alkoxy" as used herein mean those having 1 to 8, preferably 1 to 4, carbon atoms, and the same will apply hereinbelow. The most common example of the group R1 is a cyclic hydrocarbon group having 6 carbon atoms.

The protected amino group represented by the group R2 in the general formulae (1) to (3) is not particularly restricted. Examples of the protecting group thereof are as follows: (1) acyl groups, more particularly, optionally substituted lower alkanoyl groups (e.g., formyl, acetyl, propionyl and trifluoroacetyl groups); (2) urethane-forming protecting groups such as optionally substituted lower alkoxycarbonyl groups (e.g., tert-butoxycarbonyl and tert-amyloxycarbonyl groups) and optionally substituted aralkyloxycarbonyl groups (e.g., p-nitrobenzyloxycarbonyl and benzyloxycarbonyl groups); (3) optionally substituted arylsufonyl groups (e.g., tosyl group); and (4) aralkyl groups (e.g., trityl and benzyl groups). The most common examples thereof are (1) acyl groups and (2) urethane-forming protecting groups. These preferable examples are optionally substituted lower alkanoyl groups, optionally substituted lower alkoxycarbonyl groups or optionally substituted aralkyloxycarbonyl groups. The more preferable specific examples are tert-butoxycarbonyl and benzyloxycarbonyl. Examples of the protected amino group represented by the group R21 in the formula (4) include the same ones as those cited in the case of the group R2 except a phthalyl-protected amino group. Preferable examples of the hydrocarbon residues having 1 to 12 carbon atoms represented by the groups R3 and R4 are lower alkyl groups having 1 to 8, more preferably 1 to 4, carbon atoms (e.g., methyl, ethyl, propyl and butyl groups) and aryl groups. As the aryl groups, the same ones as those cited in the case of the group R1 may be cited. The preferable examples are phenyl or lower alkyl-substituted phenyl groups.

The reduction of the butyrate derivative of the general formula (1) into an alcohol can be usually effected by dissolving the compound of the general formula (1) in a solvent and then treating it with an appropriate reducing agent. Although the solvent is not particularly restricted so long as the compound (1) is soluble therein, it is preferable to use a polar solvent such as an alcohol or an ether. In general, reduction may be effected under relatively mild conditions with the use of a reducing compound of an element of the boron group such as a reducing boron compound or a reducing aluminum compound (e.g., boron hydride compound or aluminum hydride compound) or with the use of diborane. In the case of the reduction of the compound of the general formula (1) into the compound of the general formula (2) in the present invention, there is a risk that the sulfonyl group present in the molecule of the compound (1) might be reduced when a strong reducing agent is employed. Thus it is appropriate to carry out the reduction by using an alkali metal borohydride or an alkaline earth metal borohydride compound such as sodium borohydride, calcium borohydride or lithium borohydride).

The reducing agent is used in an amount of from 1 to 10 equivalents, preferably from 2 to 5 equivalents, based on the reactant. When a boron hydride compound is used as the reducing agent, for example, it may be added either in the form of a solid as such or in the form of a solution. In the case of a reducing agent which can be hardly obtained, it may be generated in situ, for example, in the reaction solution and employed in the reaction.

When sodium borohydride is to be used, a lower alcohol such as methanol, ethanol or isopropanol, or an ether such as tetrahydrofuran or a mixture thereof is used as a reaction solvent. The reaction is carried out at a temperature in the range of −20° C. to the reflux temperature of the solvent (for example, about 80° C.), preferably from 5° to 30° C.

When calcium borohydride is to be used, ethanol is employed as the solvent. In some cases, a solution of calcium chloride is added to a solution of sodium borohydride to thereby form calcium borohydride in situ which is then employed in the reaction. In such a case, the reaction is carried out at a temperature in the range of −20° C. to room temperature (30° C.), preferably from −10° to 10° C.

When lithium borohydride is to be used, an ether such as diethyl ether or tetrahydrofuran is employed as the solvent. The reaction is carried out at a temperature in the range of −10° C. to the reflux temperature of the solvent (for example, about 80° C.), preferably 20° to 30° C. so as to prevent the occurrence of side reactions.

After the completion of the reaction, the reaction mixture is treated in accordance with the conventional method to thereby give the compound of the general formula (2). For example, the reaction mixture is treated by appropriately combining procedures commonly employed in the art, concentration, extraction and crystallization. Thus the compound of the general formula (2) can be isolated. More particularly, in the case where a water-soluble alcohol solvent is used, the pH value of the reaction mixture is adjusted to 2 to 6, preferably 3 to 5, by using a mineral acid such as hydrochloric acid or an organic acid such as citric acid. After the solvent is distilled off and adding water to the residue, the target compound is extracted with a water-insoluble solvent such as ethyl acetate. Then the extract is concentrated and a solvent, in which the target compound is insoluble, is added thereto. Thus the target compound can be crystallized.

Alternatively, the compound of the general formula (2) may not be isolated but used in the subsequent step as such.

The compound of the general formula (2) is epoxidized by, for example, dissolving the compound (2) in an inert solvent and reacting it in the presence of a base to thereby induce condensation and epoxidation.

The base to be used in the epoxidation of the compound of the general formula (2) is, for example, an alkali metal compound or an alkaline earth metal compound. It is preferable to use an alkali metal alcoholate, preferably a lower alcoholate having 1 to 6 carbon atoms, such as potassium tert-butylate or sodium ethylate, an alkali metal hydride such as sodium hydride or potassium hydride, an alkali metal hydroxide such as sodium hydroxide or potassium hydroxide, or an alkali metal carbonate such as potassium carbonate or sodium carbonate. It is more preferable to use an alkali metal carbonate such as potassium carbonate or sodium carbonate from among the compounds as cited above, since the use of a strong base would sometimes induce a side reaction depending on the reaction conditions and thus lower the yield of the target product. The amount of the base is not particularly restricted. It is recommended to use the base in an amount of from 1 to 4 equivalents, preferably from 1 to 2 equivalents, based on the reactant, i.e., the compound of the formula (2) and to effect the reaction at a temperature in the range of 0° to 60° C., preferably 20° to 30° C.

As the solvent, polar solvents, for example, ketones such as acetone, ethers such as dioxane, tetrahydrofuran or ethylene glycol dimethyl ether, amides such as N,N-dimethylformamide or N,N-dimethylacetamide, lower alkyl sulfoxides such as dimethyl sulfoxide, and alcohols such as ethanol or methanol are usable. It is preferable to use a lower alcohol such as methanol. The alkali metal carbonate may be suspended in the solvent as such, or water may be added to dissolve it. After the completion of the reaction, the reaction mixture is neutralized with a dilute mineral acid such as dilute sulfuric acid or dilute hydrochloric acid or an aqueous solution of a carboxylic acid such as citric acid or acetic acid. Next, the extractant is distilled off. Thus the compound of the general formula (3) can be obtained.

Examples of the compound of the general formula (1) according to the present invention are as follows:

(1) methyl N-benzyloxycarbonyl-3(S)-amino-2(R)-p-toluenesulfonyloxy- or methanesulfonyloxy-4-phenylbutyrate;

(2) methyl N-tert-butoxycarbonyl-3(S)-amino- 2(R)-p-toluenesulfonyloxy- or methanesulfonyloxy-4-phenylbutyrate;

(3) ethyl N-benzyloxycarbonyl-3(S)-amino-2(R)-p-toluenesulfonyloxy- 4-phenylbutyrate;

(4) methyl N-tert-butoxycarbonyl-3(S)-amino- 2(R)-p-toluenesulfonyloxy-4-cyclohexylbutyrate; and (5) methyl N-benzoyl-3(S)-amino-2(R)-methanesulfonyloxy- 4-phenylbutyrate.

These compounds of the general formula (1) can be obtained by the method described in Japanese Patent Publication (Kokoku) No. 51578/1986 or in accordance therewith. Namely, in the presence of an organic base (e.g., pyridine or its derivative such as dimethylpyridine or a tertiary alkylamine such as triethylamine), an alkyl ester of an N-protected-3(S)-amino- 2(R)-hydroxy-4-$C_{3-12}$ hydrocarbon residue (e.g., phenyl or cyclohexyl)-butyric acid is reacted with a halogenoalkyl or arylsulfonyl compound (e.g., a halogenomethanesulfonyl or p-toluenesulfonyl halogenide).

Examples of the compound of the general formula (2) according to the present invention are as follows:

(1) N-benzyloxycarbonyl-3(S)-amino-2(R)-p-toluenesulfonyloxy- or methanesulfonyloxy-4-phenyl- 1-butanol;

(2) N-tert-butoxycarbonyl-3(S)-amino-2(R)-p-toluenesulfonyloxy- or methanesulfonyloxy-4-phenyl-1butanol;

(3) N-tert-butoxycarbonyl-3(S)-amino-2(R)-p-toluenesulfonyloxy- 4-cyclohexyl-1-butanol; and (4) N-benzoyl-3(S)-amino-2(R)-methanesulfonyloxy-4-phenyl-1-butanol.

Examples of the epoxy compound of the general formula (3) according to the present invention are as follows:

(1) N-benzyloxycarbonyl-3(S)-amino-1,2(S)-epoxy-4-phenylbutane;

(2) N-tert-butoxycarbonyl-3(S)-amino-1,2(S)-epoxy-4-phenylbutane;

(3) N-benzyloxycarbonyl-3(S)-amino-1,2(S)-epoxy-4-cyclohexylbutane; and (4) N-benzoyl-3(S)-amino-1,2(S)-epoxy-4-phenylbutane.

To further illustrate the present invention in detail, the following Examples will be given. However it is to be understood that the present invention is not restricted thereto.

Referential Example 1

Methyl-N-benzyloxycarbonyl-3(S)-amino-2(R)-p-toluenesulfonyloxy- 4-phenylbutyrate 20 g of methyl N-benzyloxycarbonyl-3(S)-amino- 2(R)-hydroxy-4-phenylbutyrate was dissolved in 100 ml of pyridine and 13.3 g of p-toluenesulfonyl chloride was added thereto while maintaining the reaction temperature at 10° to 20° C. Next, 0.03 g of dimethylaminopyridine (DMAP) was added thereto as a catalyst and the mixture was stirred at 20° to 25° C. for 5 hours. Then the reaction mixture was diluted with 500 ml of water and extracted with 150 ml portions of ethyl acetate twice. The extract was washed successively with 50 ml of 2 N hydrochloric acid and 50 ml of a saturated aqueous solution of sodium chloride, dehydrated over anhydrous sodium sulfate and filtered. After distilling off the solvent, 32.5 g of methyl N-benzyloxycarbonyl-3(S)-amino-2(R)-p-toluenesulfonyloxy- 4-phenylbutyrate was obtained as a pale yellow, oily substance.

Analysis for identification:
TLC: KIESELGEL® 60F254 (a product of Merck & Co., Inc.) developing soluvent; cyclohexane : ethyl acetate=1 : 1 (v/v) Rf; 0.82

Example 1

N-Benzyloxycarbonyl-3(S)-amino-2(R)-p-toluenesulfonyloxy- 4-phenyl-1-butanol 32.4 g of methyl N-benzyloxycarbonyl-3(S)-amino- 2(R)-p-toluenesulfonyloxy-4-phenylbutyrate obtained in the above Referential Example 1 was dissolved in 250 ml of ethanol and cooled to −5° to 0° C., followed by the addition of 9.03 g of sodium borohydride. Then 62.4 g of a solution of calcium chloride in ethanol, which had been prepared by dissolving 12.8 g of calcium chloride in 62 ml of ethanol, was dropped thereinto, while maintaining the reaction temperature at 0° C. or below. After stirring for 3 hours, the pH value of the reaction mixture was adjusted to 4 to 4.5 by adding a 5% aqueous solution of citric acid. After distilling off the solvent under reduced pressure, 210 ml of water was added to the concentrate. Then it was extracted with 150 ml portions of ethyl acetate twice and the extract was washed with 50 ml of a saturated aqueous solution of sodium chloride and dried over anhydrous sodium sulfate. After filtering off the sodium sulfate and distilling off the solvent under reduced pressure, 200 ml of n-hexane was added to the concentration residue for crystallization. The crystals thus precipitated were filtered and dried in vacuo. Thus 25.5 g of crude N-benzyloxycarbonyl-3(S)-amino- 2(R)-p-toluenesulfonyloxy-4-phenyl-1-butanol was obtained.

Analysis for identification:
HPLC: column; Nucleosil® 100 5 $C_{18}$ 250×4.6 mm i.d. eluent; 0.1 m $NH_4PO_4$: $CH_3CN$=1 : 1 (v/v) elution rate; 1 ml/min detection; UV 254 nm column temp.; 35° C. retention time; 11.3 min.

Example 2

N-Benzyloxycarbonyl-3(S)-amino-1,2(S)-epoxy-4-phenylbutane 25.5 g of the crude N-benzyloxycarbonyl-3(S)-amino-2(R)-p-toluenesulfonyl-4-phenyl-1-butanol obtained in the above Example 1 was dissolved in 750 ml of methanol. Then 13.9 g of potassium carbonate was added thereto at 10° C. and the resulting mixture was stirred for 3 hours at 10° to 20° C. The pH value of the reaction mixture was adjusted to 7 to 7.5 by adding a 5% aqueous solution of citric acid. After distilling off the solvent under reduced pressure, 150 ml of water was added to the concentrate. Then it was extracted with 150 ml portions of ethyl acetate twice and the extract was washed with 50 ml of a saturated aqueous solution of sodium chloride and dried over anhydrous sodium sulfate. After filtering off the sodium sulfate and distilling off the solvent under reduced pressure, 14.4 g of crude N-benzyloxycarbonyl- 3(S)-amino-1,2(S)-epoxy-4-phenylbutane was obtained.

To 14.2 g of the crude N-benzyloxycarbonyl-3(S)-amino-1,2(S)-epoxy-4-phenylbutane obtained above was added 30 ml of ethyl acetate. After dissolving at 35° to 45° C., 0.5 g of activated carbon was added thereto for decoloration. After filtering, 150 ml of n-hexane was added to the filtrate for crystallization. The crystals thus precipitated were filtered and dried in vacuo to give 13.0 g of purified N-benzyloxycarbonyl- 3(S)-amino-1,2(S)-epoxy-4-phenylbutane.

The overall yield of Referential Example 1 and Example 1 through Example 2 was 75.1%. In the HPLC analysis, no 2R,3S-isomer was detected. Analysis for identification:

HPLC: effected under the same conditions as those of Example 1 retention time; 7.0 min.
$^1$H-NMR (CDCl$_3$) δ(ppm) 2.68–3.07 (m, 5H) 3.75 (m, 1H) 4.70 ( br, 1H ) 5.04 (s, 2H) 7.15–7.40 (m, 10H). m.p.; 101°–102° C. Specific rotatory power [α]$_D$=+110° (c=1, CHCl$_3$)

Referential Example 2

Methyl-N-benzyloxycarbonyl-3(S)-amino-2(R)-methanesulfonyloxy- 4-phenylbutyrate 206 g of methyl N-benzyloxycarbonyl-3(S)-amino- 2(R)-hydroxy-4-phenylbutyrate was dissolved in 1,000 ml of methylene chloride and cooled to −10° C. After adding 79 g of triethylamine, 82.5 g of methanesulfonyl chloride was slowly added thereto under cooling at the same temperature. The obtained mixture was stirred at 15° to 0° C. for 1 hour and then 500 ml of water was added thereto to effect liquid/liquid separation. The organic layer was separated and washed successively with 1N hydrochloric acid, a 5% aqueous solution of sodium hydrogencarbonate and a saturated aqueous solution of sodium chloride and concentrated under reduced pressure. Thus 253 g of methyl N-benzyloxycarbonyl- 3(S)-amino-2(R)-methanesulfonyloxy-4-phenylbutyrate was obtained as a pale yellow, oily substance.

Analysis for identification:

HPLC: column; Inertsil® ODS 2 250×4.6 mm i.d. eluent; 0.01 M NH$_4$H$_2$PO$_4$ (pH 2.5) : CH$_3$CN =35 : 65 (v/v) other conditions were the same as those employed in Example 1 retention time; 6.0 min.

Example 3

N-Benzyloxycarbonyl-3(S)-amino-2(R)-methanesulfonyloxy- 4-phenyl-1-butanol 253 g of methyl N-benzyloxycarbonyl-3(S)-amino- 2(R)-methanesulfonyloxy-4-phenylbutyrate obtained in the above Referential Example 2 was dissolved in a solvent mixture of 1,800 ml of ethanol with 600 ml of tetrahydrofuran and cooled to −10° C. After adding 45.4 g of sodium borohydride, a solution of 66.6 g of calcium chloride in 330 ml of ethanol was dropped thereinto while maintaining the reaction temperature at 0° C. or below. After the completion of the addition, the mixture was stirred at 0° to 10° C. for 2 hours and the pH value thereof was adjusted to 3 to 4 by adding 2 N hydrochloric acid. After distilling off the solvent, water was added to the concentrate. Then it was extracted with ethyl acetate and the organic layer was washed with a saturated aqueous solution of sodium chloride and dried over anhydrous sodium sulfate. After filtering off the sodium sulfate and concentrating under reduced pressure, n-hexane was added to the residue for crystallization. The crystals thus precipitated were filtered and dried. Thus 216 g of N-benzyloxycarbonyl-3(S)-amino-2(R)-methanesulfonyloxy-4-phenyl-1-butanol was obtained in the form of white crystals.

Analysis for identification:

HPLC: effected under the same conditions as those of Referential Example 2 retention time; 4.3 min.
$^1$H-NMR (CDCl$_3$) δ(ppm) 2.77–3.10 (m, 2H) 3.08 (s, 3H) 3.60–3.90 (m, 2H) 4.31 (m, 1H) 4.76 (d, J=6.7 Hz, 1.8 Hz, 1H ) 4.98 (d like, 1H ) 5.04 (s, 2H) 7.15–7.37 (m, 10H) m.p.; 121°–122° C.

Example 4

N-Benzyloxycarbonyl-3(S)-amino-1,2(S)-epoxy-4-phenylbutane

To a suspension of 196.7 g of the N-benzyloxycarbonyl-3(S)-amino-2(R)-methanesulfonyloxy-4-phenyl- 1-butanol obtained in the above Example 3 in 2,500 ml of methanol was added 90 g of potassium carbonate. The obtained mixture was then stirred at room temperature for 5 hours. The pH value of the reaction mixture was adjusted to 7 with a 10% aqueous solution of citric acid. Then the solvent was concentrated under reduced pressure. After adding water to the residue, it was extracted with ethyl acetate. The organic layer was washed with a saturated aqueous solution of sodium chloride. After adding anhydrous sodium sulfate and activated carbon, the mixture was filtered. Then the filtrate was concentrated and n-hexane was added thereto for crystallization. The crystals thus precipitated were filtered and dried. Thus the target N-benzyloxycarbonyl-3(S)-amino-1,2(S)-epoxy-4-phenylbutane was obtained in the form of white crystals. The overall yield of Referential Example 2 and Example 3 through Example 4 was 72.3%.

Analysis for identification

HPLC: effected under the same conditions as those of Referential Example 2 excepting that, adjusting the ratio of the eluent mixture to 1 : 1 (v/v) retention time; 13.2 min.

The $^1$H-NMR data, the melting point and the specific rotatory power of this product completely agreed with those described in Example 2. In the HPLC analysis, no 2R,3S-isomer was detected.

Example 5

N-tert-Butoxycarbonyl-3(S)-1,2(S)-epoxy-4-phenylbutane 30.9 g of methyl N-tert-butoxycarbonyl-3(S)-amino-2(R)-hydroxy-4-phenylbutyrate was treated by the same method as those described in the above Referential Example 1 and Examples 1 and 2. Thus 22.3 g of N-tert-butoxycarbonyl-3(S)-1,2(S)-epoxy-4-phenylbutane was obtained in the form of white crystals (yield: 84.7%). In the HPLC analysis, no 2R,3S-isomer was detected.

Analysis for identification:

HPLC: effected under the same conditions as those of Example 1 retention time; 16.7 min.
$^1$H-NMR (CDCl$_3$) δ(ppm) 1.40 (s, 9H) 2.78–2.97 (total, 5H) 3.70 (brs, 1H) 4.45 (brs, 1H) 7.20–7.39 (m, 5H) m.p.; 123°–124° C.

Example 6

N-tert-Butoxycarbonyl-3(S)-amino-1,2(S)-amino-1,2-epoxy-4-cyclohexylbutane 15.8 g of methyl N-tert-butoxycarbonyl-3(S)-amino-2(R)-hydroxy-4-cyclohexylbutyrate was treated by the same method as those described in the above Referential Example 2 and Examples 3 and 4. Thus 12.5 g of N-tert-butoxycarbonyl-3(S)-amino-1,2(R)-epoxy-4-cyclohexylbutane was obtained in the form of a white, waxy substance (yield: 92.9%).

$^1$H-NMR (CDCl$_3$)

δ(ppm) 0.8–1.9 (m, 22H) including 1.44 (s, 9H) 2.75 (m, 2H) 2.84 (m, 1H) 3.55 (br, 1H) 4.37 (m. 1H)

We claim:

1. A process for producing an optically active erythro-3-amino-1,2-epoxy compound represented by the following general formula (3):

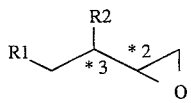  Formula (3)

wherein R1 represents a hydrocarbon residue having 3 to 12 carbon atoms; and R2 represents optionally protected amino, provided that when the carbon atom at the *3-position has an S configuration, then the carbon atom at the *2-position has an S configuration, and when the carbon atom at the *3-position has an R configuration, then the carbon atom at the *2-position has an R configuration, characterized by reducing an optically active threo-3-amino- 2-substituted butyrate derivative represented by the following general formula (1):

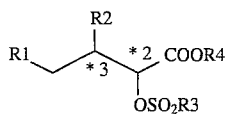  Formula (1)

wherein R1 and R2 are each as defined above; R3 represents a hydrocarbon residue having 1 to 12 carbon atoms; and R4 represents an ester residue, provided that when the carbon atom at the *3-position has an S configuration, then the carbon atom at the *2-position has an R configuration, and when the carbon atom at the *3-position has an R configuration, then the carbon atom at the *2-position has an S configuration, and then epoxidizing the obtained optically active threo-3-amino-2-substituted-1-butanol derivative represented by the following general formula (2):

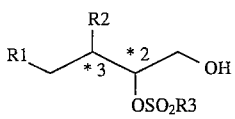  Formula (2)

wherein R1, R2, *2 and *3 are each as defined above, in the presence of a base to thereby give the target compound of the general formula (3).

2. A process as set forth in claim 1 wherein the group R1 is a hydrocarbon residue having 3 to 8 carbon atoms.

3. A process as set forth in claim 1 wherein the group R1 is a hydrocarbon residue having 6 carbon atoms.

4. A process as set forth in claim 1 wherein the group R1 is cyclohexyl or phenyl.

5. A process as set forth in any one of claims 1, 2, 3 or 7 wherein the group R2 is an amino protected by acyl groups or urethane-forming protecting groups.

6. A process as set forth in claim 5 wherein the group R2 is an amino protected by optionally substituted lower alkanoyl groups, optionally substituted lower alkoxycarbonyl groups or optionally substituted aralkyloxycarbonyl groups.

7. A process as set forth in claim 1 where in the group R1 is cyclohexyl or phenyl and the group R2 is tert-butoxycarbonyl or benzyloxycarbonyl.

8. A process as set forth in any one of claims 1, 2, 3, 4, or 7 wherein the group R3 is a lower alkyl or a lower alkyl-substituted phenyl.

9. A process as set forth in any one of claims 1, 2, 3, 4 or 7 wherein the reducing agent for the compound of the general formula (1) is a reducing compound of an element of the boron group.

10. A process as set forth in any one of claims 1, 2, 3, 4 or 7 wherein the reducing agent for the compound of the general formula (1) is a boron hydride compound.

11. A process as set forth in any one of claims 1, 2, 3, 4 or 7 wherein the compound of the general formula (2) is epoxidized in the presence of an alkali metal carbonate.

12. An optically active threo-3-amino-2-substituted-1-butanol derivative represented by the following general formula (4):

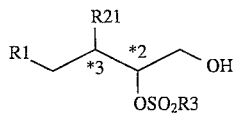  Formula (4)

wherein R1 represents a hydrocarbon residue having 3 to 12 carbon atoms; R21 represents an optionally protected amino except phthalimino; and R3 represents a hydrocarbon residue having 1 to 12 carbon atoms, provided that when the carbon atom at the *3-position has an S configuration, then the carbon atom at the *2-position has an R configuration, and when the carbon atom at the *3-position has an R configuration, then the carbon atom at the *2-position has an S configuration.

13. An optically active threo-3-amino-4-phenyl- 2-substituted-1-butanol derivative as set forth in claim 12 wherein the group R1 in the compound represented by the general formula (4) is phenyl.

14. An optically active threo-3-amino-4-phenyl- 2-substituted-1-butanol derivative as set forth in claim 12 wherein, in the general formula (4), the group R1 is phenyl or cyclohexyl, the group R21 is an amino protected by optionally substituted lower alkanoyl groups, optionally substituted lower alkoxycarbonyl groups or optionally substituted aralkyloxycarbonyl groups and the group R3 is a lower alkyl or a lower alkyl-substituted phenyl.

15. An optically active threo-3-amino-4-phenyl- 2-substituted-1-butanol derivative as set forth in claim 12 wherein, in the general formula (4), the group R1 is phenyl or cyclohexyl, the group R21 is an amino protected by tert-butoxycarbonyl or benzyloxycarbonyl.

16. A process as set forth in claim 4 wherein the group R2 is an amino protected by acyl groups or urethane-forming protecting groups, the group R3 is a lower alkyl or a lower alkyl-substituted phenyl and the reducing agent for the compound of the general formula (1) is a reducing compound of an element of the boron group.

17. A process as set forth in claim 16 wherein the group R2 is an amino protected by optionally substituted lower alkanoyl groups, optionally substituted lower alkoxycarbonyl groups or optionally substituted aralkyloxycarbonyl groups.

18. A process as set forth in claim 16 wherein the group R2 is tert-butoxy carbonyl or benzyloxycarbonyl.

19. A process as set forth in claim 16 wherein the group R2 is tert-butoxy carbonyl or benzyloxycarbonyl and the reducing agent for the compound of the general formula (1) is a boron hydride compound.

20. A process as set forth in claim 1, wherein the group R1 is cyclohexyl or benzyloxycarbonyl, the group R2 is tert-butoxy carbonyl or benzyloxycarbonyl, the group R3 is a lower alkyl or lower alkyl-substituted phenyl, the group R4 is a lower alkyl group, the reducing agent for the compound of the general formula (1) is a boron hydride compound and the compound of the general formula (2) is epoxidized in the presence of an alkali metal carbonate.

* * * * *